(12) United States Patent
Yamano

(10) Patent No.: US 8,048,374 B2
(45) Date of Patent: Nov. 1, 2011

(54) AUTOMATIC ANALYZER

(75) Inventor: Teruhiro Yamano, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 473 days.

(21) Appl. No.: 12/032,353

(22) Filed: Feb. 15, 2008

(65) Prior Publication Data

US 2008/0199358 A1 Aug. 21, 2008

(30) Foreign Application Priority Data

Feb. 19, 2007 (JP) ................................ 2007-037307

(51) Int. Cl.
*G01N 21/00* (2006.01)
*G01N 31/00* (2006.01)
*G01N 33/00* (2006.01)

(52) U.S. Cl. .......................................... 422/64; 422/63

(58) Field of Classification Search .................. None
See application file for complete search history.

(56) References Cited

U.S. PATENT DOCUMENTS

| 4,595,562 A * | 6/1986 | Liston et al. ................ 422/65 |
| 4,900,513 A | 2/1990 | Barker et al. |
| 6,444,171 B1 | 9/2002 | Sakazume et al. |
| 7,670,553 B2 * | 3/2010 | Babson ........................... 422/64 |
| 2005/0013735 A1 | 1/2005 | Gebrian et al. |
| 2005/0207938 A1 | 9/2005 | Hanawa et al. |

FOREIGN PATENT DOCUMENTS

| EP | 1 498 734 A1 | 1/2005 |
| JP | 2004061169 A * | 2/2004 |
| JP | 2005-037171 | 2/2005 |

* cited by examiner

*Primary Examiner* — Jill Warden
*Assistant Examiner* — Charles D Hammond
(74) *Attorney, Agent, or Firm* — Mattingly & Malur, PC

(57) ABSTRACT

An object of the present invention is to provide an automatic analysis method and an automatic analyzer which are suitable for improving throughput by changing reagents during analysis without placing a load on an operator, and without stopping the analysis. There is provided an automatic analysis method comprising the steps of: while moving a reagent transfer mechanism with respect to a reagent pipettor, dispensing a reagent placed in the reagent transfer mechanism by use of the reagent pipettor to cause a sample to react with the dispensed reagent; and measuring the reacted sample so as to analyze specified analysis items of the sample. A reagent is transferred from a reagent storage unit to a reagent changing mechanism. Then, the reagent changing mechanism is moved in synchronization with the reagent transfer mechanism so that reagents are changed during the synchronization.

10 Claims, 4 Drawing Sheets

AUTOMATIC ANALYZER

BACKGROUND OF THE INVENTION

1. Field of the Invention

The present invention relates to an automatic analyzer for performing qualitative/quantitative analysis of a biological sample such as blood and urine and more particularly to an automatic analyzer including a reagent cassette holding mechanism for holding a plurality of reagent cassettes.

2. Description of the Related Art

In general, for the purpose of making measurements on a plurality of analysis items, an automatic analyzer for performing qualitative/quantitative analysis of a biological sample such as blood and urine includes a reagent cassette storage unit for storing therein a plurality of reagents corresponding to the analysis items. An administrator of the automatic analyzer manages the reagent cassette storage unit so that reagents required for analysis for a day are stored. However, in the event that a reagent shortage occurs during the analysis, the analysis is temporarily interrupted to replace the reagents.

On the other hand, the number of analysis items to be analyzed by the automatic analyzer increases. Therefore, for the purpose of analyzing the other items, each reagent cassette is also miniaturized so that a large number of reagent cassettes can be placed. In this case, in comparison with the conventional analyzers, there is a higher possibility that a reagent shortage will occur during analysis. In response to the above problem, there is disclosed in JP-A-2005-37171 an automatic analyzer including a mechanism that is capable of automatically adding a reagent to a reagent cassette storage unit.

SUMMARY OF THE INVENTION

The automatic analyzer described in the JPA-2005-37171 can automatically add a reagent during analysis. However, in order to transfer the reagent from a reagent cassette temporary storage unit to a reagent cassette storage unit (reagent disk), it is necessary to temporarily stop the reagent disk; accordingly, it is also necessary to temporarily stop the analysis. In addition, after sample dispensing is stopped, the reagent disk does not stop until reagent dispensing for the dispensed sample is all completed (otherwise, the analysis of the dispensed sample cannot be completed, resulting in waste). Accordingly, the operator is forced to wait during that time.

However, because the space-saving and higher performance of automatic analyzers are achieved, the consumption of reagents per unit time during analysis increases. Moreover, because a reagent transfer mechanism continuously operates during the analysis, temporarily stopping the reagent transfer mechanism by frequently changing reagents results in decreased analysis throughput. Therefore, there is an increasing necessity to automatically perform cumbersome reagent changing without stopping the analysis.

An object of the present invention is to provide an automatic analyzer that includes a mechanism for automatically changing reagents without stopping the analysis.

In order to achieve the above-described object, according to one aspect of the present invention, there is provided an automatic analyzer that is configured as follows:

An automatic analyzer including:

a reagent cassette holding mechanism for holding a plurality of reagent cassettes, the reagent cassette holding mechanism including a mechanism for transferring an arbitrary reagent cassette to a reagent dispensing position;

a reagent cassette changing mechanism that is capable of moving in synchronization with transfer of a reagent cassette placed in the reagent cassette holding mechanism and that holds at least one reagent cassette; and a reagent cassette transfer mechanism for transferring the reagent cassette which is held by the reagent cassette changing mechanism to the reagent cassette holding mechanism.

In general, the reagent cassette holding mechanism includes a mechanism capable of transferring a reagent cassette so that an arbitrary reagent can be transferred to a reagent dispensing position. As a method for transferring a reagent cassette, various kinds of method can be applied. For example, there is a reagent cassette transfer method in which a reagent cassette is transferred, being placed on, what is called, a reagent disk or a belt conveyor. The reagent disk, or the belt conveyor, includes a mechanism for simultaneously transferring a plurality of reagent cassettes with the plurality of reagent cassettes placed on a table. The point is the reagent cassette transfer method has only to hold a plurality of reagent cassettes and to transfer an arbitrary reagent to a reagent dispensing position. The synchronization described in "capable of moving in synchronization with transfer of a reagent cassette" means enabling to transfer a reagent cassette from the reagent cassette holding mechanism to the reagent changing mechanism, or in the reverse direction, by making their transfer speeds substantially the same. Even if there is a difference in the speeds to some extent, it is to be assumed that the synchronization is made when the transfer of the reagent cassette is possible. As a method to be used by the reagent cassette transfer mechanism, there are, for example, a method that uses a belt conveyor to transfer a reagent cassette, a method that uses a nail-like mechanism to push out a reagent cassette, and a method in which a reagent cassette is held by tongs to be transferred. However, any kind of method can be adopted so long as a reagent cassette can be transferred.

The automatic analyzer according to the present invention is capable of automatically supplying the automatic analyzer with reagents without interrupting the analysis in midstream.

DETAILED DESCRIPTION OF THR PREFERRED EMBODIMENTS

Preferred embodiments of the present invention will be described with reference to drawings as below.

First Embodiment

Figure 1:
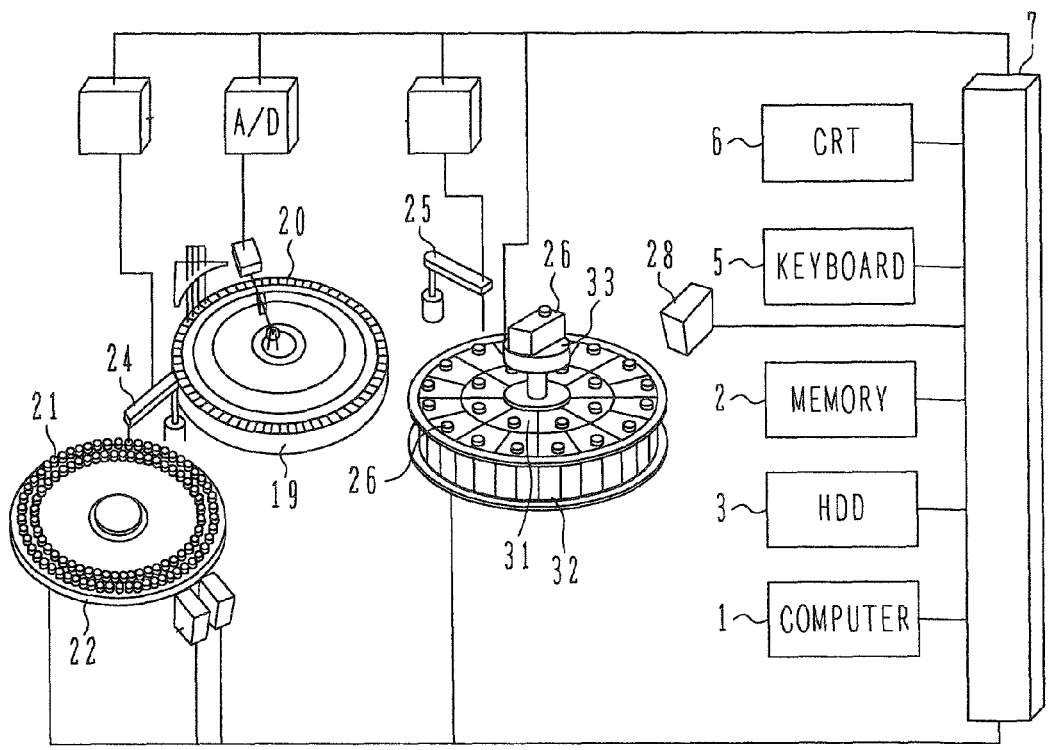
FIG. 1 is a diagram schematically illustrating the overall configuration of an automatic analyzer according to one embodiment of the present invention.

FIG. 1 is a diagram illustrating the configuration of an analyzer according to one embodiment of the present invention. It schematically illustrates the overall configuration of a multi-item chemical analyzer for analyzing a plurality of analysis items relating to a sample by a photometric measuring method.

In FIG. 1, a reagent changing mechanism 33 is located at the center of a first reagent transfer mechanism 31 and at the center of a second reagent transfer mechanism 32. A large number of reagent cassettes 26, each of which contains a reagent, are arrayed in the first reagent transfer mechanism 31 and in the second reagent transfer mechanism 32. During analysis, the reagent changing mechanism 33, a reagent pipettor 25, the first reagent transfer mechanism 31, and the second reagent transfer mechanism 32 operate via an interface 7 under the control of a microcomputer 1 that performs motion control on each mechanism and arithmetic operation of measured data. Although not illustrated, the reagent changing mechanism 33 may also be located in the outer circumferential part of the second reagent transfer mechanism 32 or at the upper or lower part of the first and second reagent transfer mechanisms 31 and 32. A memory 2, a hard disk (HDD) 3, a key board 5, and a CRT 6 are connected to the interface 7.

Figure 2:
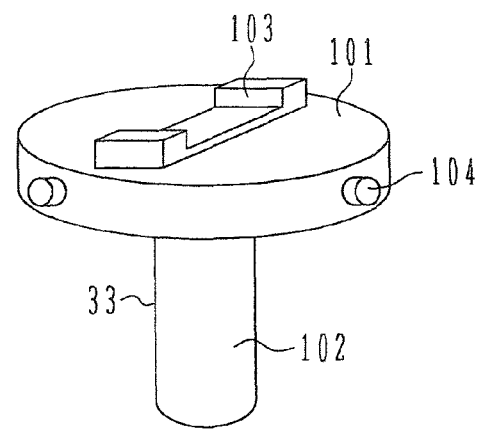
FIG. 2 is an appearance diagram illustrating an example of a reagent changing mechanism used in FIG. 1.
Figure 3:
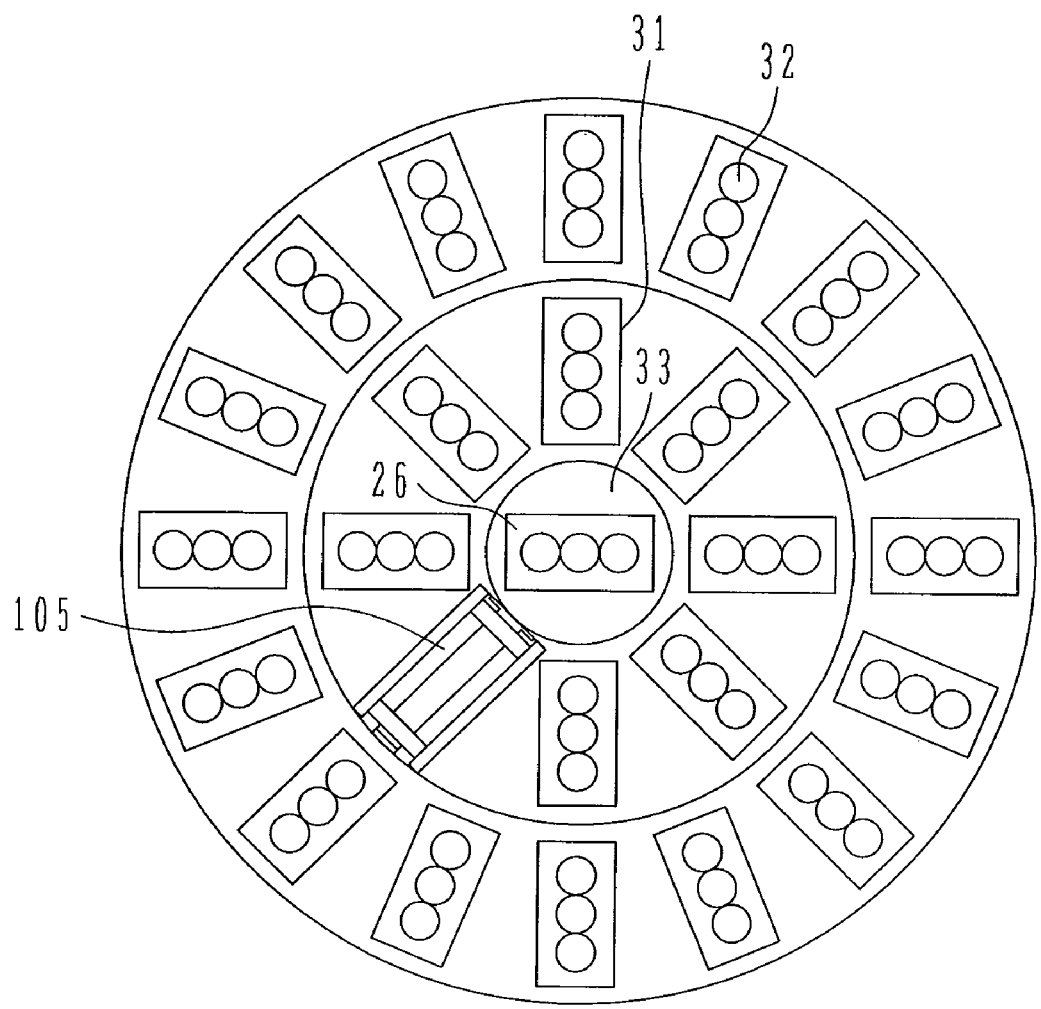
FIG. 3 is a top view (and a cross sectional view) illustrating an example of a reagent changing mechanism and a plurality of reagent transfer mechanisms, which are used in FIG. 1.
Figure 3:
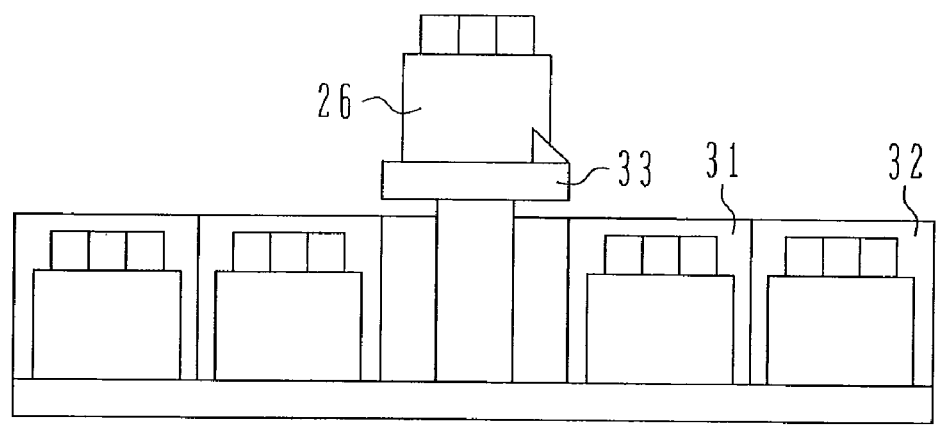
Figure 4:
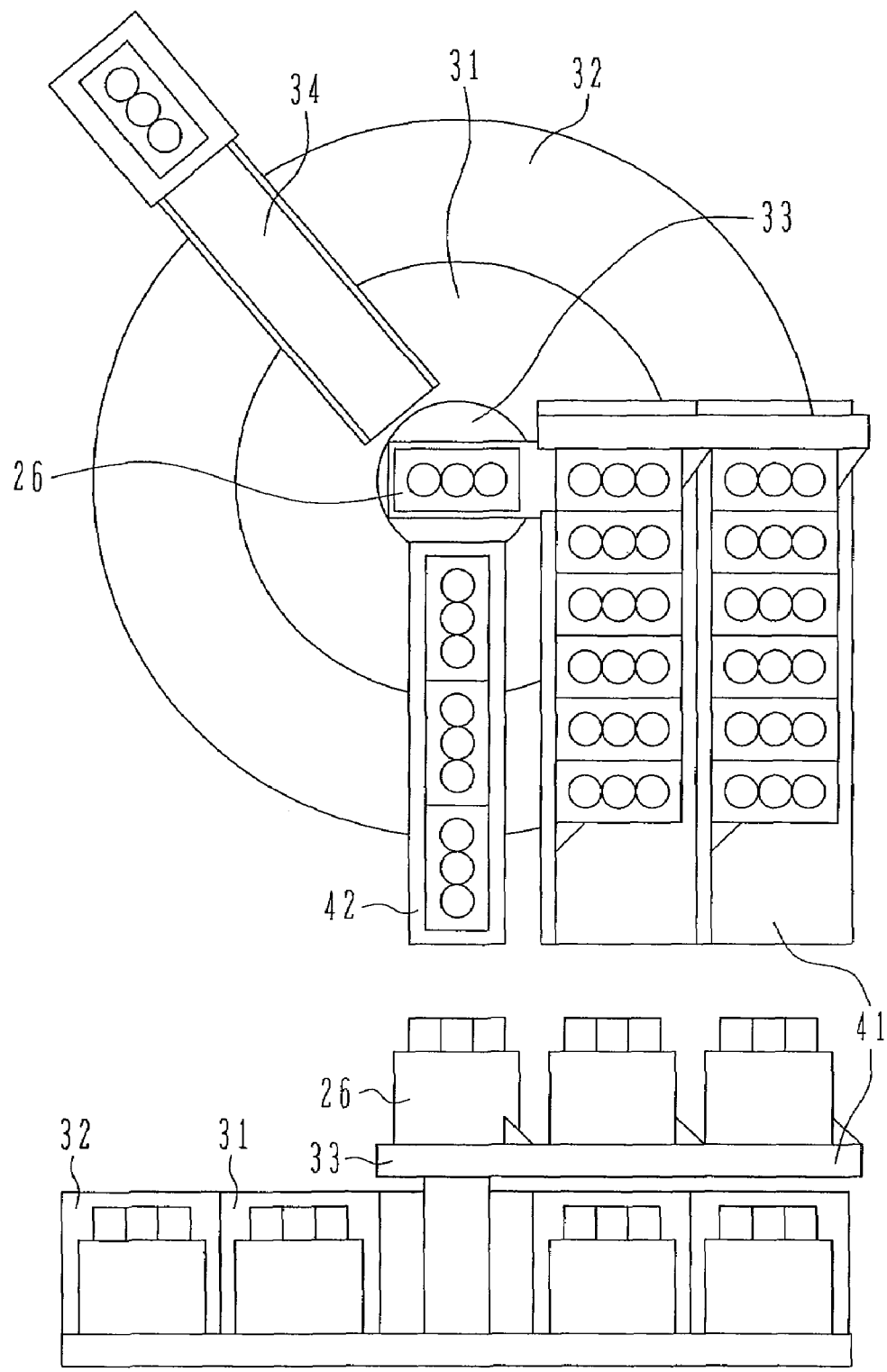
FIG. 4 is a top view (and a cross sectional view) illustrating an example of a reagent changing mechanism, a reagent charging mechanism, and a reagent discharging mechanism, which are used in FIG. 1.

As in this embodiment, if the reagent changing mechanism is located at the center of the reagent transfer mechanisms, the reagent changing mechanism 33 includes a rotator 101, a lift 102, a slider 103, and a joining unit 104 as shown in FIG. 2. In addition, as shown in FIG. 4, a reagent charging mechanism 41, a reagent discharging mechanism 42, and a reagent disposal mechanism 34 are located at the upper part of the first and second reagent transfer mechanisms 31 and 32.

During analysis, a large number of sample vessels 21, each of which contains a sample, are arrayed in a sample transfer mechanism 22. A sample which is absorbed by a sample pipettor 24 is discharged into a vessel 20 that is arrayed in a vessel transfer mechanism 19. At the same time, the first reagent transfer mechanism 31 or the second reagent transfer mechanism 32 is moved so that the reagent cassette 26 to analyze the sample is located at a position of the pipettor 25. Then, the reagent pipettor 25 absorbs a reagent and discharges the reagent into the vessel 20, thereby initiating a chemical reaction.

As a reagent charging step 1, an operator or a reagent supplying unit places the reagent cassette 26 in the reagent charging mechanism 41. When the reagent charging mechanism 41 detects that the reagent cassette 26 has been placed therein, or according to an instruction from the operator, the reagent charging mechanism 41 places each reagent cassette 26 in the reagent changing mechanism 33 one by one. If a storage medium is attached to the reagent cassette 26, reagent information may be read out by a reader 28 during this period of time preferably so as to register the height of the remaining reagent. Although not illustrated, it is desirable that the reagent charging mechanism 41 be a random access mechanism that is capable of selecting by priority a reagent cassette in which the amounts of reagents are small. In addition, although not illustrated, a package unit for packaging a reagent cassette may also be provided. If the reagent cassette is not regularly shaped, the package unit packages the reagent cassette into a rectangular parallelepiped shape so that the reagent changing mechanism can handle the reagent cassette easily.

As a reagent charging step 2, when the reagent cassette 26 is placed on the slider 103 of the reagent changing mechanism 33, the lift 102 lifts down the reagent changing mechanism 33 together with the reagent cassette 26. Next, the microcomputer 1 searches for an empty position at which no reagent cassette is placed. When the empty position is found out in the first reagent transfer mechanism 31, the rotator 101 is rotated to perform positioning control so that the empty position of the first reagent transfer mechanism 31 and the slider 103 form a straight line. Next, in order to prevent the relative positional relationship between the first reagent transfer mechanism 31 and the reagent changing mechanism 33 from deviating, the joining unit 104 is pushed out to join them together so that their synchronized transfer is assisted. If the joining unit 104 has a conical shape, they can be accurately joined together. However, if it is possible to ensure the relative positional relationship between the first reagent transfer mechanism 31 and the reagent changing mechanism 33 with a sufficiently high precision by rotation control, the joining unit 104 is not necessary. Next, the slider 103 slides the reagent cassette 26 to the empty position of the first reagent transfer mechanism 31. During this period of time, the first reagent transfer mechanism 31 may transfer the reagent cassette 26 to a position of the reagent pipettor 25 if necessary for the purpose of sample analysis. In that case, the reagent changing mechanism 33 moves as well with the relative positional relationship between the first reagent transfer mechanism 31 and the reagent changing mechanism 33 kept unchanged. This is called "synchronized transfer." When the slide operation of the reagent changing mechanism 33 ends, the joining unit 104 is pulled into the reagent changing mechanism 33, thereby completing the charging of the reagent. After the charging of the reagent ends, the lift 102 lifts up the reagent changing mechanism 33 so that the next reagent is charged.

When the empty position is found out in the second reagent transfer mechanism 32, the rotator 101 is rotated to perform positioning control so that a slider 105 of the first reagent transfer mechanism 31 and the slider 103 form a straight line. Thereafter, the same operation as that of the reagent charging step 2 is performed. The reagent cassette 26 is slid to the slider 105 of the first reagent transfer mechanism 31. Next, the first reagent transfer mechanism 31 or the second reagent transfer mechanism 32 is rotated to perform positioning control so that the slider 105 of the first reagent transfer mechanism 31 and an empty position of the second reagent transfer mechanism 32 form a straight line. Next, in order to prevent the relative positional relationship between the first reagent transfer mechanism 31 and the second reagent transfer mechanism 32 from deviating, a joining unit of the first reagent transfer mechanism 31 is pushed out to join them together so that their synchronized transfer is assisted. If it is possible to ensure the relative positional relationship between the first reagent transfer mechanism 31 and the second reagent transfer mechanism 32 with a sufficiently high precision by rotation control, the joining unit is not necessary. Next, the reagent cassette 26 on the slider 105 of the first reagent transfer mechanism 31 is slid to the empty position of the second reagent transfer mechanism 32. During this period of time, the first reagent transfer mechanism 31 or the second reagent transfer mechanism 32 may transfer the reagent cassette 26 to a position of the reagent pipettor 25 if necessary for the purpose of sample analysis. In that case, the first reagent transfer mechanism 31 and the second reagent transfer mechanism 32 are transferred in synchronization with each other. When the slide operation of the first reagent transfer mechanism 31 ends, the joining unit is pulled into the first reagent transfer mechanism 31, thereby completing the charging of the reagent. After the charging of the reagent ends, the lift 102 lifts up the reagent changing mechanism 33 so that the next reagent is charged.

As a reagent discharging step 1, when the reagent cassette 26 placed in the first reagent transfer mechanism 31 is discharged because the remaining amount of reagents becomes zero during analysis, or because the microcomputer 1 detects that an operator has issued a discharge instruction, the lift 102 lifts down the reagent changing mechanism 33, and the rotator 101 is then rotated to perform positioning control so that a position in the first reagent transfer mechanism 31 at which a reagent cassette to be discharged is placed and the slider 103 form a straight line. Next, in order to prevent the first reagent transfer mechanism 31 from positionally deviating from the reagent changing mechanism 33, the joining unit 104 is pushed out so that their synchronized transfer is assisted. After the joining, the slider 103 slides the reagent cassette to be discharged from the first reagent transfer mechanism 31 to the reagent changing mechanism 33. During this period of time, the first reagent transfer mechanism 31 may transfer the reagent cassette 26 to a position of the reagent pipettor 25 if necessary for the purpose of sample analysis. In that case, the first reagent transfer mechanism 31 and the reagent changing mechanism 33 are transferred in synchronization with each other. When the slide operation of the reagent changing mechanism 33 ends, the joining unit 104 is pulled into the reagent changing mechanism 33.

As a reagent discharging step 2, the lift 102 lifts up the reagent changing mechanism 33, and the reagent changing mechanism 33 is then rotated by the rotator 101 so that the reagent cassette 26 is slid to the reagent discharging mechanism 42, thereby completing the discharging of the reagent. In addition, it may also be configured such that reagent cassettes are classified into empty reagent cassettes and reagent cassettes with a certain amount of reagents left and that the empty reagent cassettes are slid to the reagent disposal mechanism 34.

When the reagent cassette 26 placed in the second reagent transfer mechanism 32 is discharged because the remaining amount of reagents becomes zero during analysis, or because the microcomputer 1 detects that the operator has issued a discharge instruction, the first reagent transfer mechanism 31 or the second reagent transfer mechanism 32 is rotated to perform the positioning control so that a position in the second reagent transfer mechanism 32 at which a reagent cassette to be discharged is placed and the slider 105 of the first reagent transfer mechanism 131 form a straight line. Next, in order to prevent the first reagent transfer mechanism 31 from positionally deviating from the second reagent transfer mechanism 32, the joining unit is pushed out so that their synchronized transfer is assisted. After the joining, the reagent cassette to be discharged from the second reagent transfer mechanism 32 is slid to the first reagent transfer mechanism 31. During this period of time, the first reagent transfer mechanism 31 or the second reagent transfer mechanism 32 may transfer the reagent cassette 26 to a position of the reagent pipettor 25 if necessary for the purpose of sample analysis. In that case, the first reagent transfer mechanism 31 and the second reagent transfer mechanism 32 are transferred in synchronization with each other. Next, the lift 102 lifts down the reagent changing mechanism 33, and the rotator 101 is then rotated to perform the positioning control so that the slider 105 on which the reagent cassette discharged from the first reagent transfer mechanism 31 is placed and the slider 103 form a straight line. Thereafter, the same operation as that of the discharge step 1 is performed, and the same operation as that of the discharge step 2 is performed so that the discharging of the reagent is completed.

In the first embodiment, in order to reduce the number of motors, the reagent changing mechanism 33 and the two reagent transfer mechanisms 31 and 32 are configured to be bodies of rotation. They are located such that the centers of each body of rotation share the same axis. In addition, in order to improve space efficiency, the reagent changing mechanism 33 is located at the center. Although not illustrated, it is also possible to locate three or more reagent transfer mechanisms in a similar manner. Moreover, although not illustrated, it is also possible to locate the reagent changing mechanism 33 at the outer edge of the second reagent transfer mechanism 32. In this case, it is necessary to define a slide position not in the first reagent transfer mechanism 31 but in the second reagent transfer mechanism 32.

Furthermore, although not illustrated, by locating the reagent changing mechanism 33 at the upper or lower part of the first and second reagent transfer mechanism 31 and 32, a slide position of the reagent transfer mechanism 31 or that of the reagent transfer mechanism 32 can also be eliminated.

Second Embodiment

Figure 5:
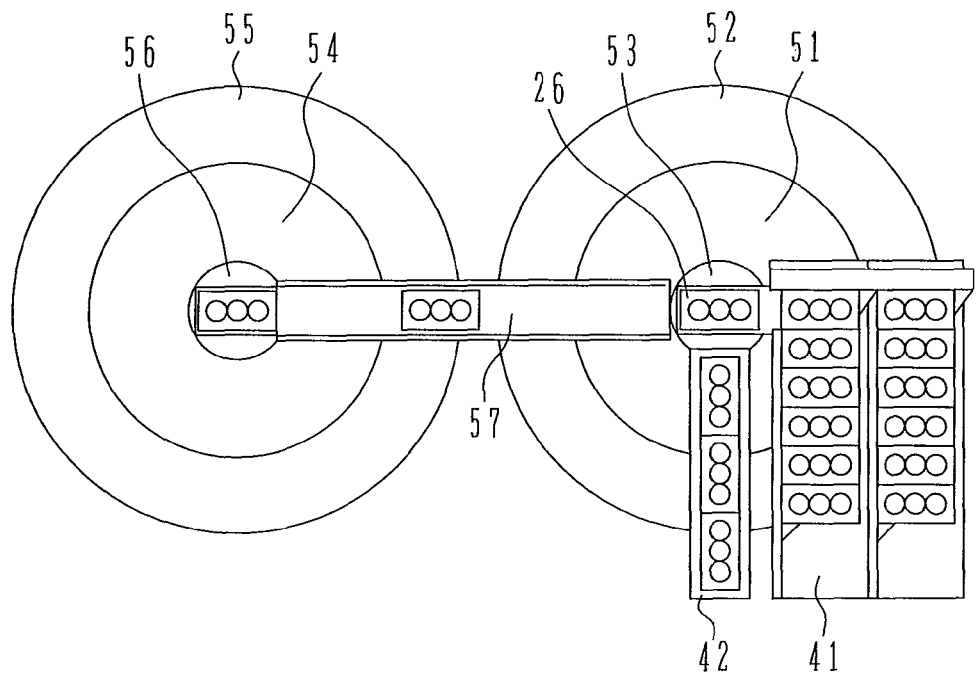
FIG. 5 is a top view illustrating an example of a plurality of reagent changing mechanisms, a reagent charging mechanism, a reagent discharging mechanism, and a bridge mechanism, which are used in FIG. 1.

FIG. 5 is a top view illustrating an automatic analyzer according to one embodiment of the present invention, the automatic analyzer including two sets of the reagent transfer mechanism and the reagent changing mechanism, the automatic analyzer further including a bridge mechanism for transferring reagents between the reagent changing mechanisms.

In FIG. 5, a first reagent changing mechanism 53 is located at the center of a first reagent transfer mechanism 51 and at the center of a second reagent transfer mechanism 52. In addition, a second reagent changing mechanism 56 is located at the center of a third reagent transfer mechanism 54 and at the center of a fourth reagent transfer mechanism 55. A bridge mechanism 57 is located between the first reagent changing mechanism 53 and the second reagent changing mechanism 56.

An operator or a reagent supply unit places a reagent cassette 26 in the reagent charging mechanism 41. When the reagent charging mechanism 41 detects that the reagent cassette 26 has been placed therein, or according to an instruction from the operator, the reagent charging mechanism 41 places each reagent cassette 26 in the first reagent changing mechanism 53 one by one. The microcomputer 1 makes comparisons among the remaining amounts of reagents in all reagent cassettes 26 placed in the first reagent transfer mechanism 51 and the second reagent transfer mechanism 52, the remaining amounts of reagents in all reagent cassettes 26 placed in the third reagent transfer mechanism 54 and the fourth reagent transfer mechanism 55, and the remaining amounts of reagents in all reagent cassettes 26 placed in the reagent charging mechanism 41, thereby determining a placement position of the reagent cassette 26 so that the reagent placement achieves the optimum analysis throughput. For example, the placement position is determined in such a manner that the remaining amounts of reagents used to analyze a particular item become equivalent. As a result, if the placement in the first reagent transfer mechanism 51 or the second reagent transfer mechanism 52 is determined, the reagent cassette 26 is transferred via the first reagent changing mechanism 53 to the first reagent transfer mechanism 51 or the second reagent transfer mechanism 52. In another case, if the placement in the third reagent transfer mechanism 54 or the fourth reagent transfer mechanism 55 is determined, the reagent cassette 26 is transferred from the first reagent changing mechanism 53 through the bridge mechanism 57 to the second reagent changing mechanism 56.

In addition, the reagent cassette 26 can also be transferred from the first reagent transfer mechanism 51 and the second reagent transfer mechanism 52 to the third reagent transfer mechanism 54 and the fourth reagent transfer mechanism 55, or from the third reagent transfer mechanism 54 and the fourth reagent transfer mechanism 55 to the first reagent transfer mechanism 51 and the second reagent transfer mechanism 52, according to intended purposes (for example, for the purpose of the reagent placement achieving the optimum analysis throughput, for the purpose of reusing expendable supplies required for maintenance, or for the purpose of following an instruction by the operator).

In the second embodiment, the automatic analyzer is configured to include the bridge mechanism 57 so as to reduce the number of reagent charging mechanisms 41 and the number of reagent discharging mechanisms 42. Although not illustrated, even if the automatic analyzer includes three or more sets of the reagent transfer mechanism and the reagent changing mechanism, it is possible to reduce the number of reagent charging mechanisms 41 and the number of reagent discharging mechanisms 42 by using the bridge mechanism 57 to make connections among them.

Figure 6:
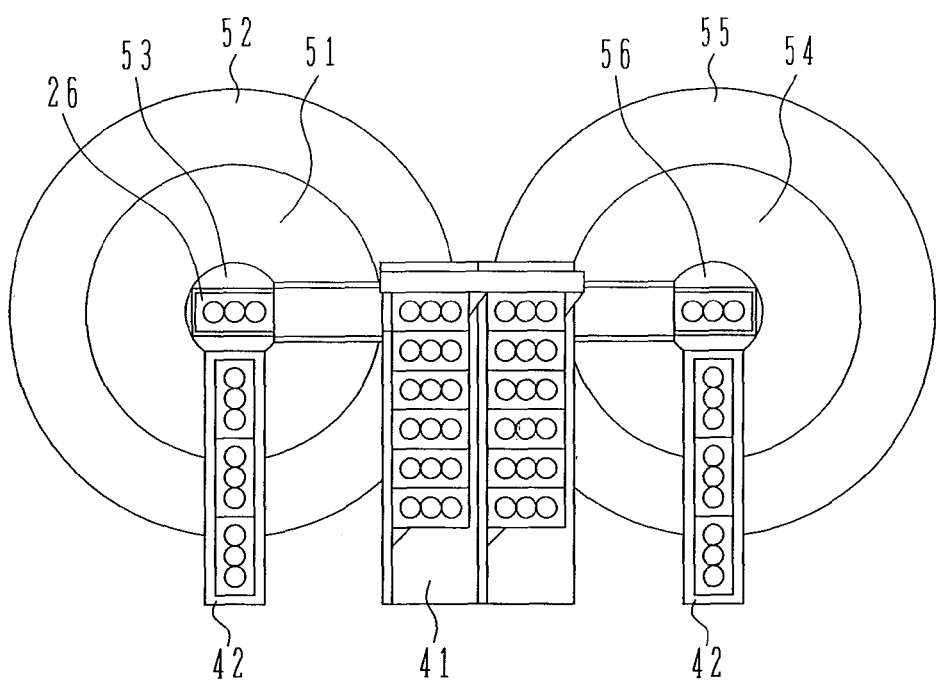
FIG. 6 is a top view illustrating an example of a plurality of reagent changing mechanism, a reagent charging mechanisms, and a reagent discharging mechanism, which are used in FIG. 1.

In addition, in FIG. 6, the first reagent changing mechanism 53 is located at the center of the first reagent transfer mechanism 51 and at the center of the second reagent transfer mechanism 52. Further, the second reagent changing mechanism 56 is located at the center of the third reagent transfer mechanism 54 and at the center of the fourth reagent transfer mechanism 55. The reagent charging mechanism 41 is located between the first reagent changing mechanism 53 and the second reagent changing mechanism 56.

In this case, the operator or the reagent supply unit places the reagent cassette 26 in the reagent charging mechanism 41. If the reagent charging mechanism 41 detects that the reagent container 26 has been placed therein, or according to an instruction from the operator, the microcomputer 1 makes comparisons among the remaining amounts of reagents in all reagent cassettes 26 placed in the first reagent transfer mechanism 51 and the second reagent transfer mechanism 52, the remaining amounts of reagents in all reagent cassettes 26 placed in the third reagent transfer mechanism 54 and the fourth reagent transfer mechanism 55, and the remaining amounts of reagents in all reagent cassettes 26 placed in the reagent charging mechanism 41, thereby determining a placement position of the reagent cassette 26 so that the reagent placement achieves the optimum analysis throughput. As a result, if the placement in the first reagent transfer mechanism 51 or the second reagent transfer mechanism 52 is determined, the reagent cassette 26 is transferred via the first reagent changing mechanism 53 to the first reagent transfer mechanism 51 or the second reagent transfer mechanism 52. In another case, if the placement in the third reagent transfer mechanism 54 or the fourth reagent transfer mechanism 55 is determined, the reagent cassette 26 is transferred via the second reagent changing mechanism 56 to the third reagent transfer mechanism 54 or the fourth reagent transfer mechanism 55.

As described above, it is also possible to eliminate the bridge mechanism 57. In addition, although not illustrated, even if the automatic analyzer includes three or more sets of the reagent transfer mechanism and the reagent changing mechanism, it is possible to make connections among them.

What is claimed is:

1. A reagent transfer apparatus of an automatic analyzer comprising:

a rotary reagent cassette transfer mechanism having a first rotating mechanism for rotating reagent cassettes to a reagent dispensing position;

a rotary reagent cassette changing mechanism for holding at least one reagent cassette having a second rotating mechanism for rotating said at least one reagent cassette held by said reagent cassette changing mechanism;

a reagent cassette sliding mechanism for moving said reagent cassette held by said reagent cassette changing mechanism to said reagent cassette transfer mechanism; and a control mechanism configured to control said first and second rotating mechanisms in a transfer operation of said at least one reagent cassette held by said reagent cassette changing mechanism such that a same relative positional relationship is maintained between said reagent cassette changing mechanism and said reagent cassette transfer mechanism, and said control mechanism being further configured to align said reagent cassette sliding mechanism with an empty position of said reagent cassette transfer mechanism wherein said reagent cassette sliding mechanism transfers said at least one reagent cassette held by said reagent cassette changing mechanism to said empty position of said reagent cassette transfer mechanism from said reagent cassette changing mechanism wherein said reagent cassette changing mechanism includes a lift for transferring a reagent cassette in up and down directions between a position supporting said at least one reagent cassette on said reagent cassette changing mechanism and a position supporting said at least one reagent cassette on said reagent cassette transfer mechanism.

2. The reagent transfer apparatus of the automatic analyzer according to claim 1, further comprising, a reagent charging mechanism for storing said reagent cassettes, wherein:

through the reagent cassette changing mechanism, a reagent cassette is transferred between the reagent charging mechanism and the reagent cassette transfer mechanism.

3. The reagent transfer apparatus of the automatic analyzer according to claim 1, wherein the reagent cassette changing mechanism is located inside the reagent cassette transfer mechanism.

4. The reagent transfer apparatus of the automatic analyzer according to claim 2, wherein the reagent cassette charging mechanism is located outside the reagent cassette transfer mechanism.

5. The reagent transfer apparatus of the automatic analyzer according to claim 1, wherein the reagent cassette changing mechanism is located at a position above the reagent cassette transfer mechanism.

6. The reagent transfer apparatus of the automatic analyzer according to claim 1, wherein the reagent changing mechanism is located at a position below the reagent cassette transfer mechanism.

7. The reagent transfer apparatus of the automatic analyzer according to claim 2, wherein the reagent charging mechanism is partitioned into at least one of a reagent charging unit, a reagent discharging unit, and a reagent disposal unit, and when a reagent cassette reaches the reagent cassette changing mechanism, the reagent cassette changing mechanism determines a destination of the reagent cassette according to an intended purpose so as to transfer the reagent cassette to the determined destination.

8. The reagent transfer apparatus of the automatic analyzer according to claim 1, further comprising:

a joining unit for physically joining the reagent cassette transfer mechanism to the reagent cassette changing mechanism and releasing said reagent cassette changing mechanism from said reagent cassette transfer mechanism joined with each other.

9. The reagent transfer apparatus of the automatic analyzer according to claim 1, further comprising:
two or more sets of the reagent cassette transfer mechanism and the reagent cassette changing mechanism; and
a bridge mechanism for transferring a reagent cassette between the reagent cassette changing mechanisms.

10. The reagent transfer apparatus of the automatic analyzer according to claim 9, further comprising:
a reagent charging mechanism that is capable of selecting one of the reagent cassette changing mechanisms to which a reagent cassette is to be transferred.

* * * * *